United States Patent [19]

Cassel et al.

[11] Patent Number: 5,639,894

[45] Date of Patent: Jun. 17, 1997

[54] CARBONYLATION OF ALLYLIC ALCOHOLS AND SYNTHESIS OF AN AMBERGRIS FRAGRANCE COMPOUND

[75] Inventors: Jonathan M. Cassel, Healdsburg; Steven M. Hoagland, San Francisco; James M. Renga, Santa Rosa, all of Calif.

[73] Assignee: Henkel Kommanditgesellschaft auf Aktien, Duesseldorf, Germany

[21] Appl. No.: 216,904

[22] Filed: Mar. 23, 1994

Related U.S. Application Data

[62] Division of Ser. No. 594,249, Oct. 9, 1990, Pat. No. 5,326,888.

[51] Int. Cl.$^6$ .................... C07D 307/92; C07C 51/12; C07C 69/76; C07C 67/36
[52] U.S. Cl. .................... 549/458; 560/8; 560/101; 560/104; 560/114; 560/207; 562/406; 562/491; 562/495; 562/498; 562/500; 562/519
[58] Field of Search .................... 549/458; 562/514, 562/500, 498, 406, 491, 495; 560/207, 8, 101, 104, 114

[56] References Cited

U.S. PATENT DOCUMENTS

| | | | |
|---|---|---|---|
| 3,655,745 | 4/1972 | Fenton | 562/519 |
| 4,189,608 | 2/1980 | Kurkov | 562/519 |
| 4,585,594 | 4/1986 | Himmele et al. | 560/8 |
| 5,326,888 | 7/1994 | Cassel et al. | 549/458 |

OTHER PUBLICATIONS

Chemical Abstract vol. 112, No. 178087, Alper, (1989), "Preparation of unsaturated carboxylic acids by carbonylation of allylic alcohols".

Primary Examiner—C. Warren Ivy
Assistant Examiner—Raymond Covington
Attorney, Agent, or Firm—Ernest G. Szoke; Wayne C. Jaeschke; Real J. Grandmaison

[57] ABSTRACT

A process for the carbonylation of allylic alcohols such as nerolidol, farnesol, or their monocyclic analogues with carbon monoxide at a pressure of at least 30 bar in the presence of a polar solvent and a palladium halide catalyst, optionally an alkali metal halide salt, and optionally an alcoholic solvent. The carbonylated product may then be reduced to the corresponding alcohol, which is cyclized in the presence of Lewis or Brönsted acids to afford an ambergris fragrance compound.

33 Claims, No Drawings

CARBONYLATION OF ALLYLIC ALCOHOLS AND SYNTHESIS OF AN AMBERGRIS FRAGRANCE COMPOUND

This application is a divisional application of application Ser. No 07/594,249 filed Oct. 9, 1990, now U.S. Pat. No. 5,326,888.

BACKGROUND OF THE INVENTION

1. Field of the Invention

This invention relates to a new process for the carbonylation of substituted allylic alcohols, and to an efficient synthesis of an ambergris fragrance compound, comprising: 1) carbonylation of the allylic alcohols nerolidol, farnesol, or their monocyclic analogues described herein; 2) reduction of the resulting carboxylic acid or ester thereof to the corresponding alcohols; and 3) cyclization of the obtained alcohols to the ambergris fragrance compound.

2. Discussion of Related Art

Allylic carbonylation is a useful synthetic route for the preparation of $\beta,\gamma$-unsaturated acids and esters. The carbonylation of readily available allylic compounds, such as allylic halides and alcohols, typically requires carbon monoxide pressures in excess of 100 bar. For example, U.S. Pat. No. 4,585,594 discloses the carbonylation of tertiary allylic alcohols with the aid of a palladium halide catalyst and a phosphine promoter at a temperature of 50°–150° C. and under a pressure of 200–700 bar. The carbonylation of allyl alcohol and/or its derivatives in the presence of a carboxylic acid solvent has been previously reported by Fenton in U.S. Pat. No. 3,655,745 and by Kurkov in U.S. Pat. No. 4,189,608. The two processes described therein are reported to give dissimilar products, methacrylic acid derivatives in the former case, and 3-butenoic acid in the latter case. These processes have not been extended to more substituted, higher molecular weight allylic substrates. The use of halide promoters in catalyst systems developed for the carbonylation of allylic compounds has been disclosed in a number of patents, for example, U.S. Pat. Nos. 3,980,671, 4,025,547, 4,140,865 and GB 1,080,867. These patents cite improvements in the carbonylation process for the production of vinyl acetic acid and its esters derived from the addition of organic and Group IVA metal halide compounds to the reaction system. Alkali metal halides may be present but are not specifically included in lists of effective promoters.

Recent advances in the carbonylation of allylic compounds under conditions of low temperature and pressure have been reported by J. Tsuji, et al. in *J. Org. Chem.* 49, 1341 (1984) and S. I. Mirahashi, et al. in *Tetrahedron Lett.* 29, 4945 (1988). Tsuji describes the carbonylation of allylic carbonates at 50° C. under a pressure of 1–20 bar of carbon monoxide. Murahashi describes the carbonylation of allylic and acetates at the same temperature under a pressure of 29–59 bar of carbon monoxide. The carbonylation of allylic acetates under these conditions is enhanced by the addition of quaternary and alkali metal halides, but lithium chloride is stated as being ineffective. The disadvantage of these mild carbonylation processes for the preparation of $\beta,\gamma$-unsaturated acids and esters via allylic alcohol derivatives is that they require one or more additional synthesis steps to convert the allylic alcohol to a more reactive derivative, and are of limited applicability for sterically hindered (e.g. tertiary) alcohols, which are difficult to quantitatively derivatize. In cases where the desired product is the $\beta,\gamma$-unsaturated carboxylic acid, carbonylation of these alcohol derivatives has the further disadvantage of necessitating a hydrolysis step, since the carbonylation product is an anhydride or ester. The carbonylation of allylic alcohols under low pressure, phase transfer conditions has been reported by H. Alper et al. in *J. Mol. Catal.* 54, L33 (1989) and EP Appl. 89 303688. This methodology, incorporating $Ni(CN)_2$ complex catalysts, has not been demonstrated to be applicable to the carbonylation of higher molecular weight allylic alcohols such as nerolidol, farnesol, monocyclonerolidol or monocyclofarnesol. Using this method, the yield of $\beta,\gamma$-unsaturated acid decreases from 53% to 36% upon changing the allylic alcohol substrate from the $C_5$ alcohol 2-methyl-3-buten-2-ol (compound A1; $CH_2=CH-CR^1R^2-OH$; $R^1=CH_3$, $R^2=CH_3$) to the $C_6$ alcohol 3-methyl-1-penten-3-ol (compound A2; $HO-CH_2-CH=CR^1R^2$; $R^1=CH_2CH_3$, $R^2=CH_3$).

The enzyme-catalyzed cyclization of trans, trans-homofarnesol (I) to 3a,6,6,9a-tetramethyldodecahydronaphtho-[2,1-b]-furan (B) has been reported by S. Neumann and H. Simon in *Biol. Chem. Hoppe-Seyler* 367, 723 (1986), but is impractical as a means of producing this material on a commercial scale. Russian patent 1,498,767 reports the reduction of (E,E)-homofarnesic acid (H; R=H) to (E,E)-homofarnesol (I) using lithium aluminum hydride, followed by cyclization of 33 mg of this alcohol with fluorosulfonic acid in 2-nitropropane at −80° to −90° C. to give (±)-3a,6,6,9a-tetramethyldodecahydronaphtho[2,1-b]furan (B). These conditions are not practical for commercial use, since they make use of extremely low temperatures, the suspected carcinogen 2-nitropropane, and a very large excess (10–15 fold) of fluorosulfonic acid, which is an extremely expensive and hazardous material. Furthermore, no evidence was given that this approach can be used on a realistic scale for the production of a commercial product.

Mixtures of 3a, 6,6,9a-tetramethyldodecahydronaphtho-[2,1-b]furan diastereomers (B) have been prepared from homofarnesic acid (G; R=H) and from its monocyclic analogue (H; R=H) by Staiger and Macri in U.S. Pat. No. 4,503,240 (1985) and by Kawanobe, et al., in *Agric. Biol. Chem.* 50, 1475 (1986), respectively. In these approaches, carboxylic acid G or H (R=H), respectively, is cyclized in the presence of acid to afford a mixture of diastereomers of tricyclic lactone K having the following structure.

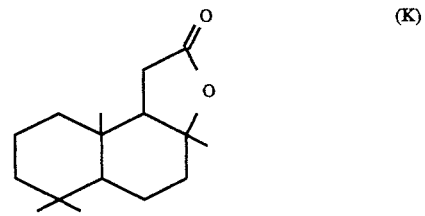

(K)

This lactone mixture is then reduced to a mixture of the corresponding diols, which is then cyclodehydrated to give a mixture of diastereomers of ambergris fragrance compound B having the structure shown herein in the following disclosure. This cyclodehydration reaction is difficult to control, and often gives large amounts of undesired side products. To avoid this, a number of approaches have been devised which give improved yields but involve the use of expensive and/or hazardous reagents. In contrast, the synthetic approach of this invention for the preparation of said compound B avoids this troublesome diol cyclodehydration step. While Russian patent 1,498,767 reports the cyclization of (E,E)-homofarnesol (I) under commercially impractical conditions, the combination of carbonylation, reduction and cyclization steps of this invention is believed to be new, and gives good yields of ambergris fragrance compound B under commercially practical conditions.

BRIEF DESCRIPTION OF THE INVENTION

Other than in the operating examples, or where otherwise indicated, all numbers expressing quantities of ingredients or reaction conditions used herein are to be understood as modified in all instances by the term "about". The terms nerolidol (C), farnesol (D), monocyclonerolidol (E), monocyclofarnesol (F), homofarnesic acid or ester (G), monocyclohomofarnesic acid or ester (H), monocyclohomofarnesol (J), norambreinolide (K), and ambergris fragrance compound B are meant to include any stereoisomer or mixture of stereoisomers unless the stereochemistry is specifically indicated. In the compound structures disclosed herein, the dotted lines indicate the possible positions of the double bond.

Initially, it should be understood that ambergris fragrance compound B represented by the following structure includes any of the diastereomers of 3a,6,6,9a-tetramethyldodecahydronaphtho-[2,1-b]-furan or any mixture of diastereomers thereof.

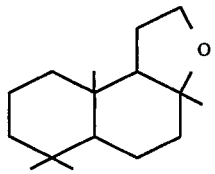
(B)

Certain diastereomers and mixtures of diastereomers of general structure B are known to have olfactory properties which are reminiscent of those of [3aR-(3aα,5aβ,9aα,9bβ)]-dodecahydro-3a,6,6,9a-tetramethylnaphtho[2,1-b]furan. This latter compound has been widely used in perfumery for many years due to its exceptional amber and woody character, and has long been commercially available as Ambroxan® (Ambroxan is a registered tradename of Henkel KGaA).

In accordance with this invention, it has now been found that it is possible to carbonylate allylic alcohols having at least five carbons and obtain acceptable yields of β,γ-unsaturated carboxylic acids or esters at carbon monoxide pressures as low as 30 bar. Such process is enabled pursuant to this invention by combination of the following principal features, namely; (1) the use of an appropriate polar solvent, (2) the elimination of phosphine ligands from the catalyst system, and optionally, (3) the addition of alkali metal halide salts to the catalyst system.

Also in accordance with this invention, an efficient synthesis of ambergris fragrance compound B has now been discovered, comprising: 1) application of the aforementioned carbonylation reaction to nerolidol (C) or farnesol (D) to afford homofarnesic acid or an ester thereof (G), or similar carbonylation of monocyclic alcohols monocyclonerolidol (E) or monocyclofarnesol (F) to afford monocyclohomofarnesic acid or an ester thereof (H), 2) reduction of compound G or H to the corresponding alcohol, i.e., homofarnesol or monocyclohomofarnesol, (I or J, respectively), and 3) cyclization of compound I or J to the ambergris fragrance compound B in the presence of a Lewis or Brönsted acid.

DETAILED DESCRIPTION OF THE INVENTION

In one embodiment of this invention there is provided a process for the carbonylation of allylic alcohols having at least five carbon atoms under the conditions described herein to provide β,γ-unsaturated carboxylic acids and esters. Preferably, the allylic alcohol is a tertiary allylic alcohol having the structure

(A1), or a primary disubstituted allylic alcohol having the structure

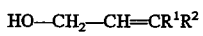
(A2), wherein $R^1$ and $R^2$ are independently alkyl, alkenyl, cycloalkyl, aryl, or arylalkyl groups having from 1 to 22 carbon atoms, to provide a β,γ-unsaturated carboxylic acid or ester thereof having the structure

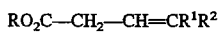
(A3), wherein $R^1$ and $R^2$ are as defined above and R is hydrogen or lower alkyl.

In another embodiment of this invention there is provided a process employing the aforementioned conditions for the carbonylation of nerolidol (C) having the structure

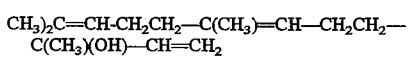
(C)

or farnesol (D) having the structure

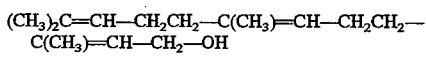
(D)

wherein nerolidol or farnesol is thereby converted to homofarnesic acid (G, R=H) or a homofarnesate ester (G, R=alkyl) having the structure

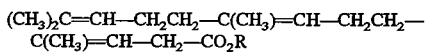
(G)

as a precursor of ambergris fragrance compound B.

In another embodiment of this invention there is provided a process employing the conditions described herein for the carbonylation of monocyclonerolidol (E) having the structure

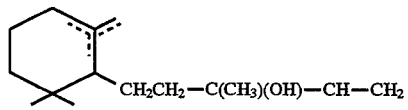
(E)

or monocyclofarnesol (F) having the structure

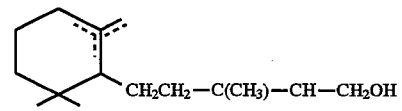
(F)

wherein compound E or F is thereby converted to monocyclohomofarnesic acid (H, R=H) or an ester thereof (H, R=alkyl) having the structure

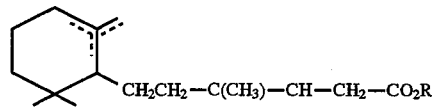
(H)

as a precursor of ambergris fragrance compound B.

In another embodiment of this invention, there is described an efficient synthesis of ambergris fragrance compound B which comprises the following steps: carbonylation of nerolidol (C), farnesol (D), monocyclonerolidol (E), or monocyclofarnesol (E) under the conditions described herein, 2) reduction of the resulting carboxylic acid (G or H, R=H) or ester thereof (G or H, R=alkyl) to the corresponding alcohol (I or J), i.e., homofarnesol (I) having the structure

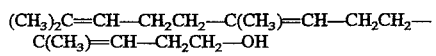
(I)

or monocyclohomofarnesol (J) having the structure

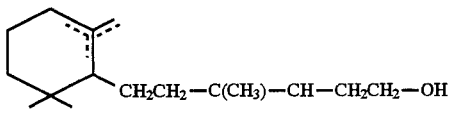

and, 3) cyclization of alcohol I or J to ambergris fragrance compound B in the presence of a Lewis or Brönsted acid. It should be understood that the disclosure of this invention is intended to include any or all stereoisomers of the aforementioned intermediate compounds.

It has been found that the carbonylation of allylic alcohols of structure A1 or A2 to β, γ-unsaturated carboxylic acids of structure A3 (R=H) at carbon monoxide pressures as low as 30 bar is enabled by employing a polar solvent and an effective amount of a palladium halide catalyst. By polar solvents is meant carboxylic acids and carboxylic acid derivatives, such as esters, amides, and nitriles, carbonic acid derivatives such as carbonates, urethanes, and ureas, and sulfoxides and sulfones. Preferred polar solvents are formic acid, acetic acid, acetonitrile, and N-methylpyrrolidinone. These preferred polar solvents have been found to enhance the carbonylation of allylic alcohols with formic acid functioning particularly well in this regard at the aforementioned pressures. Carboxylic acid solvents function in the carbonylation at levels much lower than typically employed in this type of reaction. For example, enhanced yields of carboxylic acids G (R=H) and H (R=H) can be obtained by using less than about 15 mL of these solvents per 100 grams of allylic alcohols C, D, E, or F.

It has also been found in regard to the catalyst system that whereas the prior art employs promoter ligands, specifically phosphine compounds, in the carbonylation of allylic alcohols at high pressure (i.e., over 100 bar), at lower carbon monoxide pressures, e.g., less than 100 bar, the yield of β, γ-unsaturated carboxylic acid is decreased significantly when phosphine ligand is present in a methanol or acetonitrile solution, for example. At higher carbon monoxide pressures or when carboxylic acid solvents are used, yields of β,γ-unsaturated carboxylic acids are less affected by the presence of phosphine promoter ligands.

It has also been found in regard to the catalyst system that alkali metal halide compounds promote the conversion of allylic alcohols to β,γ-unsaturated carboxylic acids in the carbonylation reaction. Alkali metal halide salts are not a necessary part of the catalyst system, but the combination of polar solvent and certain salts present in an effective amount leads to improved yields of unsaturated acid product. The preferred alkali metal salts are lithium and sodium salts, particularly the chloride compounds. When these salts are part of the catalyst system described above, the amount thereof may be 0.1 to 100 moles per mole of palladium catalyst. The preferred amount is 1 to 30 moles per mole of palladium.

In the application of the above carbonylation reaction to the synthesis of ambergris fragrance compound B, nerolidol (C), farnesol (D), or monocyclic allylic alcohols E or F is carbonylated using a palladium catalyst system with a carbon monoxide pressure of at least 30 bar either in the absence or presence of an alcoholic solvent at a temperature in the range of 50°–120° C. In the former case, it is advantageous to use formic acid as a solvent, and carboxylic acid G (R=H) or H (R=H) is obtained. If an alcoholic solvent is used, an ester (G or H; R=alkyl) is formed, for example compounds G (R=CH$_3$) or H (R=CH$_3$) when methyl alcohol is used. This ester may be hydrolyzed to the acid form. Satisfactory carbonylation results are obtained when the polar solvent is present in an amount of from about 0.01 mole to 4 mole per mole of allylic alcohol. The preferred amount thereof is preferably from 0.1 to 2 moles of polar solvent per mole of allylic alcohol. When an alcoholic solvent is present in the carbonylation step, the amount thereof can be from about 1.0 to about 10 moles alcoholic solvent per mole of allylic alcohol, and is preferably from about 1–4 moles alcoholic solvent per mole of allylic alcohol. Further, the amount of palladium halide, preferably palladium chloride, providing satisfactory results in the carbonylation step may be from about 0.0001 mole to about 0.1 mole per mole of allylic alcohol. The preferred amount is from about 0.001 mole to about 0.05 mole of palladium halide per mole of allylic alcohol. When an alkali metal halide promoter is present the amount can be from 0.1 mole to about 100 mole per mole of palladium, and is preferably from 1 to 30 moles per mole of palladium in the catalyst.

The next step in the synthesis of compound B of this invention is reduction of either compound G (R=H or alkyl) or H (R=H or alkyl) with a metal hydride reagent. If the carbonylation is run in the absence of an alcoholic solvent, the carboxylic acid produced (G or H, with R=H) can be directly reduced to the corresponding alcohol I or J, or else converted to an ester (G or H, with R=alkyl) by standard procedures and then subsequently reduced to alcohol I or J. Alternatively, if the carbonylation is run in the presence of an alcoholic solvent, an ester (G or H, with R=alkyl) is produced, which can either be reduced to the corresponding alcohol (I or J, respectively) or else hydrolyzed by standard procedures to the free acid and then reduced. A variety of different metal hydride reagents are commonly used for the reduction of carboxylic acids and esters in the presence of carbon-carbon double bonds and, in principle, any of these can be used for the conversion of compounds G and H to alcohols I and J, respectively. These metal hydride reagents include, but are not limited to, lithium aluminum hydride, diisobutylaluminum hydride, lithium trimethoxyaluminum hydride, sodium borohydride, sodium bis(2-methoxyethoxy)aluminum hydride, and lithium triethylborohydride.

In the final step of the synthesis of ambergris fragrance compound B of this invention, alcohol I or J is treated with either Lewis or Brönsted acids and is thus cyclized to compound B. A wide variety of acidic reagents have been found capable of effecting this transformation, including boron trihalides and complexes thereof and various sulfonic acids. Preferred catalysts are trifluoromethanesulfonic acid, boron trifluoride, boron trifluoride complexes, and alkyl- or arylsulfonic acids. This cyclization reaction can be run at temperatures ranging from –110° C. to +150° C. and, while a variety of solvents can be used, halocarbon solvents are preferred. In contrast to the 10 to 15-fold molar excess of fluorosulfonic acid described in Russian patent 1,498,767, it is preferred to carry out the cyclization step of this invention with at least 1.0, and as much as 5 molar equivalents of the acidic cyclization reagent. While this is the preferred range of molar equivalents of acid, the reaction can also be carried out with from 0.1 to 100 molar equivalents of acid.

Thus, the synthesis of ambergris fragrance compound B disclosed herein comprises the steps of (1) the carbonylation of nerolidol (C), farnesol (D), or monocyclic alcohols E or F with carbon monoxide at a pressure of at least 30 bar in the presence of a palladium catalyst, a carboxylic acid or other polar solvent, either together with or in the absence of an alkali metal halide salt, and optionally, in the presence or in the absence of an alcoholic solvent to give either compound G or compound H, (2) reduction of said compounds G or H with a metal hydride reducing agent to give corresponding alcohols I or J, respectively, and (3) cyclization of said alcohols I or J to compound B in the presence of an acidic reagent.

To further illustrate the present invention, the following specific examples are given, it being understood that this is merely intended in an illustrative and not a limitative sense. In the examples, all parts and percents are by weight unless otherwise indicated.

EXAMPLE I

Carbonylation of Nerolidol in Acetonitrile

Nerolidol (100 g., 0.45 moles of >98% pure material), acetonitrile (50 mL) and palladium chloride (0.50 g., 2.8 mmol) were combined in a 300 mL autoclave. The reactor was sealed and the air inside was displaced by three successive fill/vent cycles with 10 bar of carbon monoxide. The autoclave was then pressurized to 35 bar with CO while stirring the contents mechanically at 1000 rpm. Heating was started at this time. When the temperature of the reactor contents had reached the set point (90° C), the autoclave was pressurized to the reaction pressure of 69 bar with CO. A constant pressure in the reactor was maintained by auxiliary ballast tanks charged with CO. The carbonylation was allowed to continue for a period of 20 hours. The product was removed from the reactor and the autoclave was rinsed with acetone. The product and the acetone rinses were filtered. The filtrate was concentrated with a rotary evaporator. The crude homofarnesic acid was partitioned between 500 mL of ether and 1.2 L of 5% NaOH. Two layers formed. The lower layer was discarded. The upper layer was diluted with 1 L of water. The top layer of the resulting two-phase mixture was discarded. The bottom layer was extracted with ether. The ether extract was discarded. The remaining material was acidified to pH 1 with 125mL of 20% $H_2SO_4$ and extracted twice with 500 mL of ether. The combined ether extracts were washed with water until the pH of the wash solution was between 6 and 7. The ether solution was dried over $MgSO_4$, filtered and concentrated at reduced pressure to afford 59.7 g (53% mass yield) of 92 GC area % homofarnesic acid.

EXAMPLE II

Carbonylation of "Natural" Nerolidol in Acetic Acid

The carbonylation of "natural" nerolidol (100 g, 89% pure material) was performed in acetic acid (30 mL) according to the procedure detailed in Example I. The yield of isolated material was 48.4 g (43% mass yield) of 93 GC area % homofarnesic acid.

EXAMPLE III

Carbonylation of trans-Nerolidol in Formic Acid trans-Nerolidol (100 g, 0.45 moles), palladium(II) chloride (0.50 g, 2.8 mmol), lithium chloride (1.20 g, 28 mmol) and formic acid (10 mL of an 88% solution in water were charged into a 300 mL autoclave. The autoclave was sealed and the contents were heated with stirring at 1000 rpm. The air was flushed out of the reactor head space by means of three fill/vent cycles with 10 bar of carbon monoxide. The autoclave was then charged with 62 bar of carbon monoxide. When the reactor contents had reached the set point temperature of 85° C., the carbon monoxide pressure was adjusted to 69 bar. This pressure was maintained by auxiliary ballast tanks charged with carbon monoxide. The carbonylation reaction was allowed to proceed for a period of 20 hours. The contents of the autoclave were cooled to ambient temperature and the unreacted carbon monoxide was vented. The reaction mixture was filtered and washed with 100 mL of water. The crude homofarnesic acid was dissolved in 200 mL of 5% aqueous NaOH. Carbonylation side products were removed from the mixture by two extractions with 200 mL of ether. The aqueous homofarnesic acid salt was acidified with 20% $H_2SO_4$. The upper organic layer that separated was removed and set aside. The aqueous layer was extracted with 150 mL of ether. The ether layer was combined with the organic acid layer and washed with water and brine until the wash solution was near pH 6. The semi-pure homofarnesic acid was dried over $MgSO_4$. The solution was filtered and concentrated to afford 67 g (60% mass yield) of 92 GC area % homofarnesic acid.

EXAMPLE IV

Carbonylation of Farnesol in Formic Acid

Farnesol (100 g, 0.45 moles), palladium(II) chloride (0.50 g, 2.8 mmol), lithium chloride (1.20 g, 28 mmol) and formic acid (10 mL of an 89% solution in water) were charged into a 300 mL autoclave. The autoclave was sealed and the contents were heated with stirring at 500 rpm. The air was flushed out of the reactor head space by means of three fill/vent cycles with 10 bar of carbon monoxide. The autoclave was then charged with 172 bar of carbon monoxide. When the reactor contents had reached the set point temperature of 100° C., the carbon monoxide pressure was adjusted to 200 bar. This pressure was maintained by auxiliary ballast tanks charged with carbon monoxide. The carbonylation reaction was allowed to proceed for a period of 21 hours. The contents of the autoclave were cooled to ambient temperature and the unreacted carbon monoxide was vented. Analysis of the crude reaction mixture (GC area %) showed complete consumption of the farnesol, several components corresponding to farnesyl formates, and 36.6% of homofarnesic acid isomers.

EXAMPLE V

Carbonylation of Nerolidol, Comparative Examples

The carbonylation of nerolidol was performed according to the procedure in Example III, except the initial charge of CO to the autoclave was 172 bar and the final operating pressure was adjusted to 200 bar. The stir rate was 500 rpm and the total reaction time was 5 h. Qualitative analysis of the reaction mixture by GC showed a product distribution of 10.4% nerolidol and 80.4% homofarnesic acid. The crude reaction mixture was filtered then washed with 100 mL of water. The organic layer was dissolved in 200 mL of 5% NaOH and the resulting solution was extracted with ether in a continuous extractor. The aqueous layer was acidified according to Example III and 88.3 g of homofarnesic acid was isolated in the usual manner.

This reaction was repeated, except formic acid and LiCl were omitted and 1.50 g of triphenylphosphine was added to the reaction mixture. Qualitative analysis of the reaction mixture by GC showed a product distribution of 77.3% nerolidol and 20.4% homofarnesic acid.

EXAMPLE VI

Carbonylation of Nerolidol: Effect of Alkali Metal Chlorides

The carbonylation of nerolidol was performed according to the procedure in Example III except that CO reaction pressure was 200 bar, stir rate was 500 rpm, and reaction time was 5 h. In three separate reactions, LiCl, NaCl, and KCl was added as a chloride source. The effect of the cation on the product distribution and homofarnesic acid yield is tabulated below.

| Chloride | percent nerolidol | percent homofarnesic acid | mass yield (g) |
|---|---|---|---|
| Li | 10.4 | 80.4 | 88.3 |
| Na | 12.5 | 74.7 | 75.7 |
| K | 67.5 | 31.7 | not detmd. |

EXAMPLE VII

Carbonylation of Monocyclonerolidol

Monocyclonerolidol (162 g, 0.71 moles), palladium(II) chloride (0.83 g, 4.7 mmols), lithium chloride (1.90 g, 44.8 mmol), and formic acid (17 mL of a 91% solution in water) were charged into a 300 mL steel autoclave. The reactor was sealed and the contents were heated with stirring at 500 rpm. The air was flushed out of the reactor head space by means of three fill/vent cycles with 10 bar of carbon monoxide. The autoclave was then charged with 96 bar of carbon monoxide. When the reactor contents had reached the set point temperature of 85° C., the carbon monoxide pressure was adjusted to 103 bar. This pressure was maintained by auxiliary ballast tanks charged with carbon monoxide. The carbonylation reaction was allowed to proceed for a period of 22 h. The contents of the autoclave were cooled to ambient temperature and the unreacted carbon monoxide was vented. The reaction mixture was filtered. The filtrate was washed with 150 mL of water. The organic layer was dissolved in 400 mL of 5% NaOH and extracted five times with 200 mL portions of ether. The aqueous layer was acidified with 20% $H_2SO_4$. The resulting layers were separated and the top, organic layer was set aside. The lower, aqueous layer was extracted with 150 mL of ether. The organic portions were combined and washed with water and brine. The washed solution was dried over $MgSO_4$. The drying agent was removed by filtration and the filtrate was concentrated with a rotary evaporator to afford 53.6 g of 72 GC area % monocyclohomofarnesic acid.

EXAMPLE VIII

Carbonylation of Nerolidol in Methanol

Nerolidol was carbonylated according to the procedure in Example III, except that the stir rate was 500 rpm and 50 mL of methanol solvent was added to the initial charge. Qualitative analysis of the reaction mixture by capillary GC showed a product distribution of 45% methyl homofarnesate, 7% homofarnesic acid, and 20% unreacted nerolidol.

EXAMPLE IX

Carbonylation of Nerolidol with Syngas

The carbonylation of nerolidol was performed according to Example III, except the stir rate was 500 rpm and synthesis gas (1:1 mixture of $CO/H_2$) was employed as the carbon monoxide source. The reactor was initially pressurized to 110 bar with syngas and the operating pressure was 138 bar. Qualitative analysis of the reaction mixture after a period of 20 h showed a product distribution of 23% homofarnesic acid and 42% unreacted nerolidol.

EXAMPLE X

Conversion of Methyl Homofarnesate to Homofarnesol

To a solution of 10.00 g (37.8 mmol) of methyl homofarnesate in 40 mL of hexane at 0° C. was added dropwise 83 mL (83 mmol) of a 1M solution of diisobutylaluminum hydride in toluene. The resulting solution was stirred at 0° C. for 1 hour and then poured into cold 1% aqueous HCl solution and diluted with hexane. The organic layer was washed with 1% aqueous HCl solution, saturated aqueous $NH_4Cl$ solution, and brine; dried over $MgSO_4$; and concentrated in vacuo to give 6.92 g (77%) of homofarnesol as a colorless liquid.

EXAMPLE XI

Conversion of Methyl Monocyclohomofarnesate To Monocyclohomofarnesol

A solution of 10.00 g (37.8 mmol) of methyl monocyclo homofarnesate in 40 mL of hexane at 0° C. is added dropwise 83 mL (83 mmol) of a 1M solution of diisobutylaluminum hydride in toluene. The resulting solution is stirred at 0° C. for 1 hour and then poured into cold 1% aqueous HCl solution and diluted with hexane. The organic layer is washed with 1% aqueous HCl solution, saturated aqueous $NH_4Cl$ solution, and brine; dried over $MgSO_4$; and concentrated in vacuo to give the desired monocyclohomofarnesol.

EXAMPLE XII

Conversion of Homofarnesic Acid to Homofarnesol

A solution of homofarnesic acid (529 g, 2.11 moles) in toluene (2.5 L) was cooled to 0° C. in an ice bath. To this solution was cautiously added 1.25 kg of a 3.4M solution of sodium bis(2-methoxyethoxy)aluminum hydride. After the addition was complete, the reduction was allowed to proceed at ambient temperature for a period of 16 h, then heated to 100° C. for 1 h. After cooling the mixture back down to room temperature, excess reducing agent was carefully quenched with 10% NaOH. The crude reaction mixture was washed with 3 L of 10% NaOH. The organic layer was washed with brine until the pH of the wash solutions was near 6, and was then dried over $MgSO_4$ and concentrated by rotary evaporation to afford 524 g of crude homofarnesol. This material was distilled at reduced pressure through an 8 inch vigreux column. One fraction was collected: bp 90°–150° C. at 0.1–0.3 torr, 363 g (73%) of pure homofarnesol.

EXAMPLE XIII

Conversion of Monocyclohomofarnesic Acid (H, R=H) to Monocyclohomofarnesol

A solution of monocyclohomofarnesic acid (529 g, 2.11 moles) in toluene (2.5 L) is cooled to 0° C. in an ice bath. To this solution is cautiously added 1.25 kg of a 3.4M solution of sodium bis(2-methoxyethoxy)aluminum hydride. After the addition is complete, the reduction is allowed to proceed at ambient temperature for a period of 16 h then heated to 100° C. for 1 h. After cooling the mixture back down to room temperature, excess reducing agent is carefully quenched with 10% NaOH. The crude reaction mixture is washed with 3 L of 10% NaOH. The organic layer is washed with brine until the pH of the wash solutions was near 6, and is then dried over $MgSO_4$ and concentrated by rotary evaporation to afford the desired monocyclohomofarnesol.

EXAMPLE XIV

Cyclization of Homofarnesol (I) to Compound (B)

To a solution of 44.1 g (186 mmol) of homofarnesol in 400 mL of dry $CH_2Cl_2$ at -78° C. was added 18.2 mL (205 mmol) of trifluoromethanesulfonic acid, and the resulting solution was stirred at -78° C. for 40 minutes. The reaction was then quenched at this temperature by addition of 34 mL (250 mmol) of triethylamine and the solution was concentrated in vacuo. The residue was dissolved in 1 L of hexane, washed with $H_2O$, 5% aqueous HCl, and saturated aqueous $NaHCO_3$; dried over $MgSO_4$; and concentrated in vacuo to give 42.72 g of crude product. Kugelrohr distillation (0.060–0.055 torr, 50°–90° C.) gave 32.35 g (73%) of distilled product.

EXAMPLE XV

Conversion of Homofarnesol (I) To Compound B

To a solution of 1,002 g of homofarnesol in 8 mL of $CH_2Cl_2$ at 0° C. was added dropwise 1.0 mL of $BF_3 \cdot OEt_2$, and the resulting solution was stirred at 0° C. for 1 h. The reaction was then quenched by addition of 2.4 mL of triethylamine, and the resulting solution was diluted with ether, washed with $H_2O$, 1% aqueous HCl, and saturated aqueous $NaHCO_3$. The solution was then dried over $MgSO_4$ and concentrated to give 0.967 g of crude product.

EXAMPLE XVI

Conversion of Monocyclohomofarnesol (J) To Compound B

To a solution of 1.002 g of monocyclohomofarnesol in 8 mL of $CH_2Cl_2$ at 0° C. is added dropwise 1.0 mL of $BF_3 \cdot OEt_2$, and the resulting solution is stirred at 0° C. for 1 h. The reaction is then quenched by addition of 2.4 mL of triethylamine, and the resulting solution is diluted with ether, washed with $H_2O$, 1% aqueous HCl, and saturated aqueous $NaHCO_3$. The solution is then dried over $MgSO_4$ and concentrated to give the desired product.

EXAMPLE XVII

Conversion of Homofarnesol to Compound B

To a solution of 1.008 g of homofarnesol in 8 mL of $CH_2Cl_2$ at 0° C. was added 0.55 mL of methanesulfonic acid, and the resulting solution was stirred at 0° C. for 1 h. The reaction was then quenched by addition of 2.4 mL of triethylamine, and the resulting solution was diluted with ether, washed with $H_2O$, 1% aqueous HCl and saturated aqueous $NaHCO_3$. The resulting solution was dried over $MgSO_4$ and concentrated to give 0.954 g of crude product.

What is claimed is:

1. The process of preparing a β,γ-unsaturated carboxylic acid comprising carbonylating an allylic alcohol selected from the group consisting of nerolidol, monocyclonerolidol, farnesol and monocyclofarnesol with carbon monoxide at a pressure of at least about 30 bar in the presence of a polar solvent and an effective amount of a palladium halide catalyst.

2. The process in accordance with claim 1 wherein there is also present an effective amount of alkali metal halide salt.

3. The process in accordance with claim 2 wherein the amount present of said alkali metal halide salt is from about 0.1 to about 100 moles per mole of palladium catalyst in the carbonylation.

4. The process in accordance with claim 2 wherein the amount present of alkali metal halide salt is from about 1 to about 30 moles per mole of palladium.

5. The process in accordance with claim 1 wherein said β,γ-unsaturated carboxylic acid has the structure $RO_2C$—$CH_2$—$CH$=$CR^1R^2$ wherein $R^1$ and $R^2$ are independently alkyl, alkenyl, cycloalkyl, aryl, or arylalkyl groups having from 1 to 22 carbons and R is hydrogen.

6. The process in accordance with claim 1 wherein said nerolidol comprises trans-nerolidol, cis-nerolidol, and mixtures thereof.

7. The process in accordance with claim 1 wherein said farnesol is selected from trans, trans-farnesol and mixtures of farnesol stereoisomers.

8. The process in accordance with claim 1 wherein said polar solvent is selected from the group consisting of carboxylic acids and carboxylic acid derivatives.

9. The process in accordance with claim 1 wherein said polar solvent is selected from formic acid, acetic acid, acetonitrile, and N-methylpyrrolidinone.

10. The process in accordance with claim 1 wherein the amount present of said polar solvent is from about 0.01 to about 4 moles per mole of said allylic alcohol.

11. The process in accordance with claim 1 wherein the amount present of said polar solvent is from about 0.1 to about 2 moles per mole of said allylic alcohol.

12. The process in accordance with claim 1 wherein said palladium halide catalyst comprises palladium chloride.

13. The process in accordance with claim 1 wherein the amount of palladium present is from about 0.0001 to about 0.1 mole per mole of said allylic alcohol.

14. The process in accordance with claim 1 wherein the amount of palladium present is from about 0.001 mole to about 0.05 mole per mole of said allylic alcohol.

15. The process in accordance with claim 2 wherein said alkali metal halide salt comprises lithium chloride.

16. The process in accordance with claim 2 wherein said alkali metal halide salt comprises sodium chloride.

17. The process of preparing a β,γ-unsaturated carboxylic acid ester comprising carbonylating an allylic alcohol selected from the group consisting of nerolidol, monocyclonerolidol farnesol, one monocyclofarnesol with carbon monoxide at a pressure of at least about 30 bar in the presence of a polar solvent and an effective amount of a palladium halide catalyst.

18. The process in accordance with claim 17 wherein there is also present an effective amount of alkali metal halide salt.

19. The process in accordance with claim 17 wherein said β,γ-unsaturated carboxylic acid ester has the structure $RO_2C$—$CH_2$—$CH$=$CR^1R^2$ wherein $R^1$ and $R^2$ are independently alkyl or alkenyl groups having from 1 to 22 carbons and R is a lower alkyl group.

20. The process in accordance with claim 17 wherein said nerolidol comprises trans-nerolidol, cis-nerolidol, and mixtures thereof.

21. The process in accordance with claim 17 wherein said farnesol is selected from trans, trans-farnesol and mixtures of farnesol stereoisomers.

22. The process in accordance with claim 17 wherein said polar solvent is selected from the group consisting of carboxylic acids and carboxylic acid derivatives.

23. The process in accordance with claim 17 wherein said polar solvent is selected from formic acid, acetic acid, acetonitrile, and N-methylpyrrolidinone.

24. The process in accordance with claim 17 wherein the amount present of said polar solvent is from about 0.01 to about 4 moles per mole of said allylic alcohol.

25. The process in accordance with claim 17 wherein the amount present of said polar solvent is from about 0.1 to about 2 moles per mole of said allylic alcohol.

26. The process in accordance with claim 17 wherein said palladium halide catalyst comprises palladium chloride.

27. The process in accordance with claim 17 wherein the amount of palladium present is from about 0.0001 to about 0.1 mole per mole of said allylic alcohol.

28. The process in accordance with claim 17 wherein the amount of palladium present is from about 0.001 mole to about 0.05 mole per mole of said allylic alcohol.

29. The process in accordance with claim 17 wherein the molar ratio of said alcoholic solvent to said allylic alcohol is from about 1.0 to about 10.

30. The process in accordance with claim 17 wherein the molar ratio of said alcoholic solvent to said allylic alcohol is from about 1 to about 4.

31. The process in accordance with claim 17 wherein said alcoholic solvent comprises methyl alcohol.

32. The process in accordance with claim 17 including hydrolyzing the carbonylated product to the acid form.

33. An ambergris fragrance compound having the structure (B)

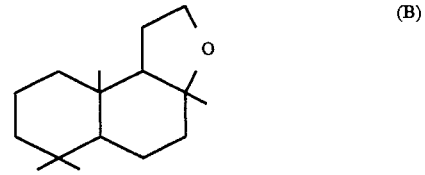

produced by the steps comprising carbonylating an allylic alcohol selected from the group consisting of nerolidol, farnesol, monocyclonerolidol, and monocyclofarnesol with carbon monoxide at a pressure of at least about 30 bar in the presence of a polar solvent and an effective amount of a palladium halide catalyst, either in the presence or absence of an alcoholic solvent; reducing the carbonylated product, either as the acid form or as the ester, to homofarnesol or monocyclohomofarnesol; and treating the reduced product under acid-catalyzed conditions to undergo direct cyclization.

* * * * *